US011940399B2

(12) United States Patent
Walsworth et al.

(10) Patent No.: US 11,940,399 B2
(45) Date of Patent: Mar. 26, 2024

(54) SYSTEMS AND METHODS FOR QUANTUM SENSING USING SOLID-STATE SPIN ENSEMBLES

(71) Applicants: University of Maryland, College Park, College Park, MD (US); The President and Fellows of Harvard College, Cambridge, MA (US)

(72) Inventors: Ronald Walsworth, Newton, MA (US); Nithya Arunkumar, Waltham, MA (US); Connor Hart, Columbia, MD (US); Dominik Bucher, Puchheim (DE); David Glenn, Cambridge, MA (US)

(73) Assignees: University of Maryland, College Park, College Park, MD (US); The President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/829,551

(22) Filed: Jun. 1, 2022

(65) Prior Publication Data
US 2023/0084726 A1    Mar. 16, 2023

Related U.S. Application Data

(60) Provisional application No. 63/197,309, filed on Jun. 4, 2021, provisional application No. 63/195,591, filed on Jun. 1, 2021.

(51) Int. Cl.
*G01N 24/00*    (2006.01)
*G01N 24/08*    (2006.01)
*G01N 33/38*    (2006.01)

(52) U.S. Cl.
CPC .......... *G01N 24/006* (2013.01); *G01N 24/08* (2013.01); *G01N 33/381* (2013.01)

(58) Field of Classification Search
CPC .... G01N 24/006; G01N 24/08; G01N 33/381; G01R 33/032; G01R 33/26;
(Continued)

(56) References Cited

U.S. PATENT DOCUMENTS 10,228,429 B2 *    3/2019    Bruce .................... G01R 33/26
10,914,800 B2 *    2/2021    Acosta .................. G01R 33/60
(Continued)

OTHER PUBLICATIONS

Jiang et al., "Repetitive Readout of a Single Electronic Spin via Quantum Logic with Nuclear Spin Ancillae", Science, vol. 326, Oct. 9, 2009, pp. 267-272.
(Continued)

*Primary Examiner* — Jay Patidar
(74) *Attorney, Agent, or Firm* — George Likourezos; Carter, DeLuca & Farrell LLP

(57) ABSTRACT

Systems and methods of quantum sensing include obtaining information regarding a target signal in electronic spin states of quantum defects in an ensemble of quantum defects, mapping the information regarding the target signal from the electronic spin states of the quantum defects to corresponding nuclear spin states associated with the quantum defects, applying a light pulse to the ensemble of quantum defects to reset the electronic spin states of the quantum defects, and repeating a readout stage a plurality of times within a readout duration. The readout stage includes mapping the information regarding the target signal back from the nuclear spin states to the corresponding electronic spin states and applying a data acquisition readout pulse to optically measure the electronic spin states of the quantum defects.

20 Claims, 5 Drawing Sheets

(58) Field of Classification Search
CPC ..... G01R 33/323; A61B 3/0075; A61B 3/103; A61B 3/107; A61B 3/1208
See application file for complete search history.

(56) References Cited

U.S. PATENT DOCUMENTS

| | | | | |
|---|---|---|---|---|
| 2014/0327439 | A1* | 11/2014 | Cappellaro | G01N 24/08 324/304 |
| 2015/0009746 | A1* | 1/2015 | Kucsko | G11C 13/04 365/152 |
| 2015/0090033 | A1* | 4/2015 | Budker | G01R 33/46 73/504.05 |

OTHER PUBLICATIONS

Neumann et al., "Single-Shot Readout of a Single Nuclear Spin", Science, vol. 329, Jul. 30, 2010, pp. 542-544.
Lovchinsky et al., "Nuclear Magnetic Resonance Detection and Spectroscopy of Single Proteins Using Quantum Logic", Science, vol. 351, Feb. 19, 2016, pp. 836-841.
Glenn et al., "High-Resolution Magnetic Resonance Spectroscopy Using a Solid-State Spin Sensor", Nature, vol. 555, Mar. 15, 2018, pp. 351-364.
Zhou et al., "Quantum Metrology with Strongly Interacting Spin Systems", Physical Review X 10, 031003 (2020), 9 pages.
Choi et al., "Robust Dynamic Hamiltonian Engineering of Many-Body Spin Systems", Physical Review X 10, 031002 (2020), 27 pages.
Taylor et al., "High-sensitivity diamond magnetometer with nanoscale resolution", Nature Physics vol. 4, Oct. 2008, pp. 810-816.
John F. Barry, "Sensitivity optimization for NV-diamond magnetometry", Rev. Mod. Phys., vol. 92, No. 1, Published Mar. 31, 2020, pp. 015004-1 to 015004-68.
Staudacher et al., Nuclear Magnetic Resonance Spectroscopy on a (5-Nanometer)3 Sample Volume, Science, vol. 339, Feb. 1, 2013, pp. 561-563.
Mamin et al., "Nanoscale Nuclear Magnetic Resonance with a Nitrogen-Vacancy Spin Sensor", Science, vol. 339, Feb. 1, 2013, pp. 557-560.
Müller et al., "Nuclear magnetic resonance spectroscopy with single spin sensitivity", Nature Communications, vol. 5, 4703, Aug. 2014, pp. 1-6.
Sushkov et al., "Magnetic Resonance Detection of Individual Proton Spins Using Quantum Reporters", Physical Review Letters, vol. 113, Nov. 7, 2014, pp. 197601-1-197601-5.
Aslam et al., "Nanoscale nuclear magnetic resonance with chemical resolution", Science, vol. 357, Jul. 7, 2017, pp. 67-71.
Glenn et al., "High-resolution magnetic resonance spectroscopy using a solid-state spin sensor", Nature, vol. 555, Mar. 15, 2018, 14 pages.
Bucher et al., "Hyperpolarization-Enhanced NMR Spectroscopy with Femtomole Sensitivity Using Quantum Defects in Diamond", Phys. Rev. X 10, 2020, pp. 021053-1-021053-9.
Adams et al., "Reversible Interactions with para-Hydrogen Enhance NMR Sensitivity by Polarization Transfer", Science, vol. 323, Mar. 27, 2009, pp. 1708-1711.
Rayner et al., "Delivering strong 1H nuclear hyperpolarization levels and long magnetic lifetimes through signal amplification by reversible exchange", PNAS, Apr. 4, 2017, pp. E3188-E3194.
Theis et al., "Zero-field NMR enhanced by parahydrogen in reversible exchange", J Am Chem Soc, 2012, 134, 9, pp. 3987-3990.
Gong et al., "Trace Analysis by Low-Field NMR: Breaking the Sensitivity Limit", Analytical Chemistry, vol. 82, No. 17, Sep. 1, 2010, pp. 7078-7082.
Theis et al., "Microtesla SABRE Enables 10% Nitrogen-15 Nuclear Spin Polarization", J. Am. Chem. Soc. 2015, 137, pp. 1404-1407.

Bucher et al., "Quantum diamond spectrometer for nanoscale NMR and ESR spectroscopy", Nature Protocols, vol. 14, Sep. 2019, pp. 2707-2747.
Badilita et al., "Microscale nuclear magnetic resonance: a tool for soft matter research", Soft Matter, 2012, vol. 8, pp. 10583-10597.
Colell et al., "Generalizing, Extending, and Maximizing Nitrogen-15 Hyperpolarization Induced by Parahydrogen in Reversible Exchange", J. Phys. Chem. C 2017, 121, pp. 6626-6634.
Troung et al., "15N Hyperpolarization by Reversible Exchange Using SABRE-SHEATH", J. Phys. Chem. C, 2015, vol. 119, pp. 8786-8797.
Lehmkuhl et al., "SABRE polarized low field rare-spin spectroscopy", J. Chem. Phys. 152, 2020, pp. 184202-1-184202-9.
Canto et al., "The NAD+ Precursor Nicotinamide Riboside Enhances Oxidative Metabolism and Protects against High-Fat Diet-Induced Obesity", Cell Metabolism, vol. 15, Jun. 6, 2012, pp. 838-847.
Knecht et al., "Re-polarization of nuclear spins using selective SABRE-INEPT", Journal of Magnetic Resonance 287, 2018, pp. 10-14.
Atkinson et al., "Para-Hydrogen Induced Polarization without Incorporation of Para-Hydrogen into the Analyte", Inorganic Chemistry, 2009, vol. 48, No. 2, pp. 663-670.
Theis et al., "LIGHT-SABRE enables efficient in-magnet catalytic hyperpolarization", Journal of Magnetic Resonance, vol. 248, 2014, pp. 23-26.
Roy et al., "Direct enhancement of nitrogen-15 targets at high-field by fast ADAPT-SABRE", Journal of Magnetic Resonance, vol. 285, pp. 2017 55-60.
Svyatova et al., "15N MRI of SLIC-SABRE Hyperpolarized 15N-Labelled Pyridine and Nicotinamide", Chemistry A European Journal, 2019, vol. 25, pp. 8465-8470.
Pravdivtsev et al., "RF-SABRE: A Way to Continuous Spin Hyperpolarization at High Magnetic Fields", The Journal of Physical Chemistry B, 2015, vol. 119, pp. 13619-13629.
Theis et al., "Quasi-Resonance Signal Amplification by Reversible Exchange", The Journal of Physical Chemistry Letters, 2018, vol. 9, pp. 6136-6142.
Ariyasingha et al., "Quasi-Resonance Fluorine-19 Signal Amplification by Reversible Exchange", The Journal of Physical Chemistry Letters, 2019, vol. 10, pp. 4229-4236.
Bordonali et al., "Parahydrogen based NMR hyperpolarisation goes micro: an alveolus for small molecule Chemosensing", Lab Chip, 2019, vol. 19, pp. 503-512.
Smits et al., "Two-dimensional nuclear magnetic resonance spectroscopy with a microfluidic diamond quantum sensor", Science Advances, Jul. 26, 2019, vol. 5: eaaw7895, 7 pages.
Rayner et al., "Signal Amplification by Reversible Exchange (SABRE): From Discovery to Diagnosis", Angew. Chem. Int. Ed., 2018, vol. 57, pp. 6742-6753.
Iali et al., "Using parahydrogen to hyperpolarize amines, amides, carboxylic acids, alcohols, phosphates, and carbonates", Science Advances, Jan. 5, 2018, vol. 4, eaao6250, 6 pages.
Bucher et al., "Hyperpolarization-Enhanced NMR Spectroscopy with Femtomole Sensitivity Using Quantum Defects in Diamond", Physical Review X 10, 021053 (2020), 9 pages.
Cowley et al., "Iridium N-Heterocyclic Carbene Complexes as Efficient Catalysts for Magnetization Transfer from para-Hydrogen", Journal of the American Chemical Society, vol. 133, Apr. 6, 2011, pp. 6134-6137.
Theis et al., "Zero-Field NMR Enhanced by Parahydrogen in Reversible Exchange", Journal of the American Chemical Society, vol. 134, Feb. 14, 2012, pp. 3987-3990.
Smits et al., "Two-Dimensional Nuclear Magnetic Resonance Spectroscopy with a Microfluidic Diamond Quantum Sensor", Science Advances, vol. 5, Jul. 26, 2019, 7 pages.
Rayner et al., "Signal Amplification by Reversible Exchange (SABRE): From Discovery to Diagnosis", Angew. Chem. Int. Ed., vol. 57, 2018, pp. 6742-6753.

* cited by examiner

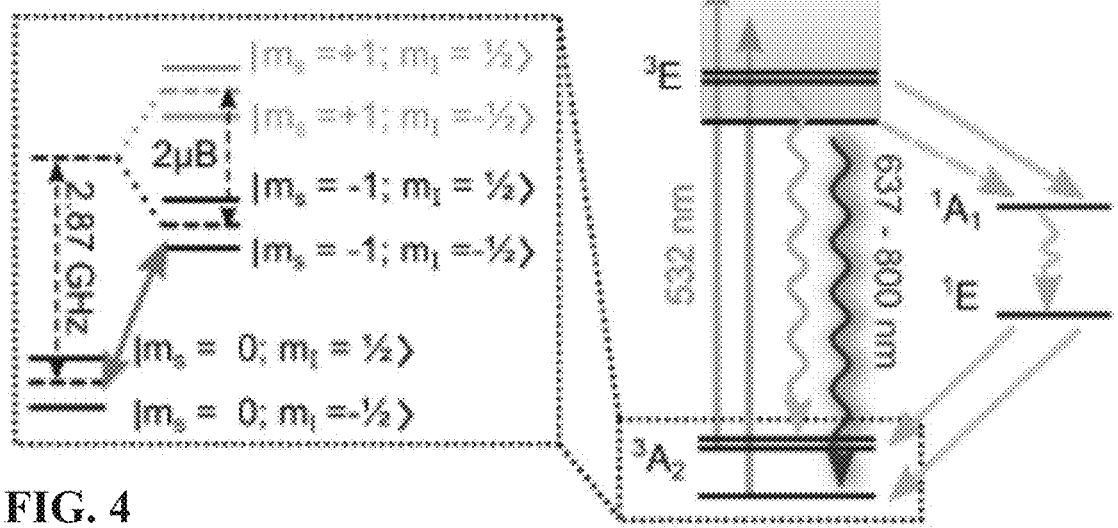
FIG. 4
FIG. 3
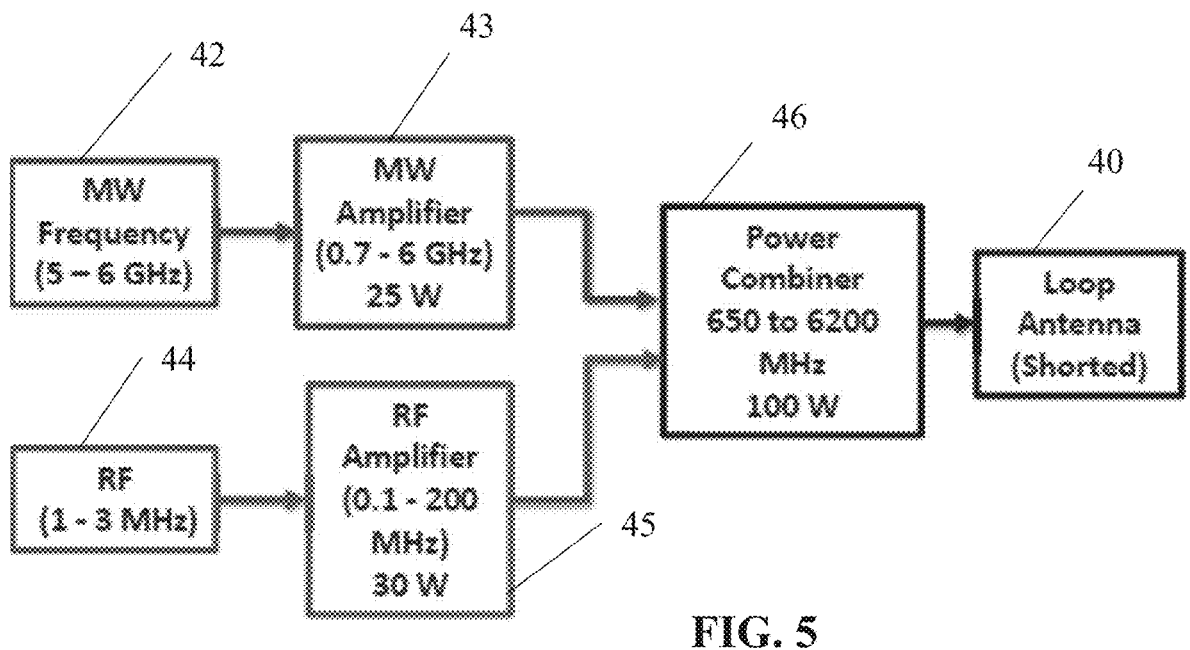
FIG. 5

SYSTEMS AND METHODS FOR QUANTUM SENSING USING SOLID-STATE SPIN ENSEMBLES

CROSS-REFERENCE TO RELATED APPLICATION

This application claims the benefit of and priority to U.S. Provisional Patent Application Ser. Nos. 63/195,591 (filed on Jun. 1, 2021) and 63/197,309 (filed on Jun. 4, 2021), the entire contents of which are hereby incorporated by reference herein. This application also incorporates by reference, in its entirety, the U.S. Non-Provisional patent application filed concurrently herewith, which also claims the benefit of and priority to U.S. Provisional Patent Application Ser. Nos. 63/195,591 and 63/197,309.

STATEMENT REGARDING FEDERALLY SPONSORED RESEARCH/DEVELOPMENT

This invention was made with government support under W911NF-19-2-0181, and W911NF-15-1-0548 awarded by the Army Research Laboratory—Army Research Office. The government has certain rights in the invention.

FIELD

The present disclosure relates to quantum sensing and, more specifically, to systems, methods, and devices for quantum sensing using solid-state spin ensembles, e.g., nitrogen-vacancy (NV) center ensembles in diamond.

BACKGROUND

Optically-probed solid state quantum defects such as nitrogen-vacancy (NV) centers in diamond enable the detection of magnetic signals. As a result, an NV center ensemble in diamond is a prominent candidate for quantum sensing applications, e.g., in biological and material sciences, especially under ambient conditions. For example, quantum sensing may find applicability in nuclear magnetic resonance (NMR), integrated circuits, magnetic microscopy, crystal stress and pressure spectroscopy, thermometry, and/or other areas.

A quantum memory technique facilitating quantum sensing was first realized in a single NV system in 2009 and later utilized for NMR spectroscopy of a single protein. However, this technique has yet to be extended to NV center ensembles, due to technical differences between single NV centers and NV center ensembles.

SUMMARY

Provided in accordance with aspects of the present disclosure is a method of quantum sensing including obtaining information regarding a target signal in electronic spin states of quantum defects in an ensemble of quantum defects, mapping the information regarding the target signal from the electronic spin states of the quantum defects to corresponding nuclear spin states associated with the quantum defects, applying a light pulse to the ensemble of quantum defects to reset the electronic spin states of the quantum defects, and repeating a readout stage a plurality of times within a readout duration. The readout stage includes mapping the information regarding the target signal back from the nuclear spin states to the corresponding electronic spin states and applying a data acquisition readout pulse to optically measure the electronic spin states of the quantum defects.

In an aspect of the present disclosure, obtaining the information includes applying a light pulse to the ensemble of quantum defects to polarize the electronic spin states of the quantum defects, and performing a sensing sequence to obtain the information regarding the target signal in the electronic spin states of the quantum defects. The sensing sequence may include, for example and without limitation, an XY decoupling sequence; a correlation spectroscopy sequence; or a DROID-60 decoupling sequence. Other suitable sensing sequences include, for example and without limitation, T1 relaxometry, Ramsey sequences, and strain-CPMG sequences (e.g., for sensing non-magnetic sources like lattice strain in the diamond, pressure, or temperature).

In another aspect of the present disclosure, mapping the information regarding the target signal from the electronic spin states of the quantum defects to the corresponding nuclear spin states associated with the quantum defects includes applying a microwave (MW) pulse and a radio frequency (RF) pulse to the ensemble of quantum defects.

In yet another aspect of the present disclosure, mapping the information regarding the target signal back from the nuclear spin states to the corresponding electronic spin states includes applying an MW pulse to the ensemble of quantum defects.

In still another aspect of the present disclosure, the readout stage further includes, after applying the MW pulse, applying a light pulse to the ensemble of quantum defects to repolarize the electronic spin states of the quantum defects. Application of the light pulse generates fluorescence that can be optically measured. Indeed, in still yet another aspect of the present disclosure, the method further includes determining the information regarding the target signal based upon the optical measuring (e.g., of the fluorescence) in the plurality of readout stages.

In aspects of the present disclosure, the ensemble of quantum defects includes an ensemble of nitrogen vacancy (NV) centers in diamond. The number of quantum defects in the ensemble of quantum defects may be at least on the order of $10^4$, at least on the order of $10^6$, or at least on the order of $10^8$. Additionally or alternatively, the NV center density may be about 1 ppm.

In another aspect of the present disclosure, the information regarding the target signal includes information regarding a magnetic field signal, e.g., an AC or DC magnetic field signal.

In still another aspect of the present disclosure, the method includes applying a magnetic bias field to the ensemble of quantum defects during the obtaining, the mapping, the applying, and the repeating. The magnetic bias field may have a magnitude significantly different from 51.2 mT; in aspects, the magnitude is at least 3×, 5×, or 7× the magnitude of 51.2 mT. Additionally or alternatively, the magnetic bias field has a range of less than about 100 uT across the spatial extent of the NV center ensemble.

A quantum sensor provided in accordance with the present disclosure includes an ensemble of quantum defects and at least one controller including at least one processor and at least one associated memory storing instructions to be executed by the processor to cause the at least one controller to perform any of the methods detailed herein. In particular, the controller may be caused to direct application of a sensing sequence of energy pulses to the ensemble of quantum defects to obtain information regarding a target signal in electronic spin states of quantum defects in an ensemble of quantum defects, direct application of a microwave (MW) pulse and a radio frequency (RF) pulse to the ensemble of quantum defects to map the information regarding the target signal from the electronic spin states of the quantum defects to corresponding nuclear spin states associated with the quantum defects, direct application of a light pulse to the ensemble of quantum defects to reset the electronic spin states of the quantum defects, and direct repetition of a readout stage a plurality of times within a readout duration. In each readout stage, the controller is caused to direct application of an MW pulse to the ensemble of quantum defects to map the information regarding the target signal back from the nuclear spin states to the corresponding electronic spin states, and direct application of a data acquisition readout pulse to the ensemble of quantum defects to optically measure the electronic spin states of the quantum defects, e.g., by measuring fluorescence from excitation of the NC center by the light pulse.

In an aspect of the present disclosure, the at least one controller is further caused to direct application of a light pulse to the ensemble of quantum defects to polarize the electronic spin states of the quantum defects prior to the sensing sequence.

In another aspect of the present disclosure, the at least one controller is further caused to direct application of a light pulse to the ensemble of quantum defects to repolarize the electronic spin states of the quantum defects after the MW pulse in each readout stage.

In still another aspect of the present disclosure, the ensemble of quantum defects includes an ensemble of nitrogen vacancy (NV) centers in diamond.

In yet another aspect of the present disclosure, the information regarding the target signal includes information regarding a magnetic field signal.

In still yet another aspect of the present disclosure, the at least one controller is further caused to direct application of a magnetic bias field to the ensemble of quantum defects at a magnitude significantly different from 51.2 mT; in aspects, the magnitude is at least 3×, 5×, or 7× the magnitude of 51.2 mT. Additionally or alternatively, the magnetic bias field has a range of less than about 100 uT across the spatial extent of the NV center ensemble.

To the extent consistent, any of the aspects and/or features detailed herein may be used in conjunction with any or all of the other aspects and/or features described herein.

BRIEF DESCRIPTION OF THE DRAWINGS

Various aspects and features of the present disclosure are described hereinbelow with reference to the drawings wherein:

FIG. 3 illustrates the NV center energy levels allowing optical readout of electronic spin states;

FIG. 4 is an enlarged illustration of the area of detail indicated in FIG. 3 showing the state triplet energy levels splitting due to Zeeman and hyperfine interactions;

FIG. 5 is a block diagram illustrating microwave (MW) and radio frequency (RF) energy sources coupled to the loop antenna of the system of FIG. 1;

DETAILED DESCRIPTION

The present disclosure provides systems, methods, and devices for quantum sensing (e.g., AC or DC magnetometry) using solid-state spin ensembles, e.g., nitrogen-vacancy (NV) center ensembles in diamond. Other suitable solid-state spin ensembles include, for example and without limitation, quantum defect ensembles in silicon carbide, hexagonal boron nitride, and rare-earth doped crystals such as $Ce^{3+}$ in a yttrium aluminum garnet crystal. More specifically, the present disclosure leverages the two-qubit system (electronic spin and nuclear spin) of each NV center in an ensemble of NV centers in diamond, utilizing the electronic spins of the NV centers as sensor/readout qubits and the nearby nuclear spins as memory qubits. That is, sensed information captured in the electronic spin in each negatively charged NV center in the ensemble is mapped (entangled and swapped) onto the nearby $^{15}N$ nuclear spin, thus enabling storage of the information for sufficient time to allow for repetitive optical readout performed by repeatedly re-mapping (re-entangling and re-swapping) the information stored in the $^{15}N$ nuclear spin onto the electronic spin and optically measuring the electronic spin. Although detailed herein with respect to an ensemble of negatively charged NV centers in diamond, the present disclosure is applicable for use with any other suitable defect centers in solid-state ensembles that enable the above-noted two-qubit functionality.

The present disclosure also solves the technical challenges introduced when moving from a single NV center system to an NV center ensemble. In particular, the present disclosure utilizes a homogeneous NV center ensemble in diamond, a homogeneous external magnetic field, homogeneous microwave (MW) and radio frequency (RF) pulses (at appropriate speeds and powers), homogeneous optical pulses, and homogeneous NV electronic spin properties. As a result, the nuclear memory spin lifetime is maximized (thus enabling a greater number of readouts) and all of the NV centers (two-qubit systems) in the ensemble are maintained sufficiently identical to permit global control of the spin states, thereby enabling high fidelity.

The result of the above is a quantum sensor system that provides a factor of 30 improvement in signal-to-noise ratio and sensitivity enhancement exceeding an order of magnitude. Aspects and features of the quantum sensor systems and methods of the present disclosure are described in greater detail below. Although detailed herein with respect to quantum magnetometry, the aspects and features of the present disclosure are also applicable for use in other suitable quantum sensing applications such as, for example, crystal stress and pressure spectroscopy, thermometry, and/or other areas.

Figures 1, 2:
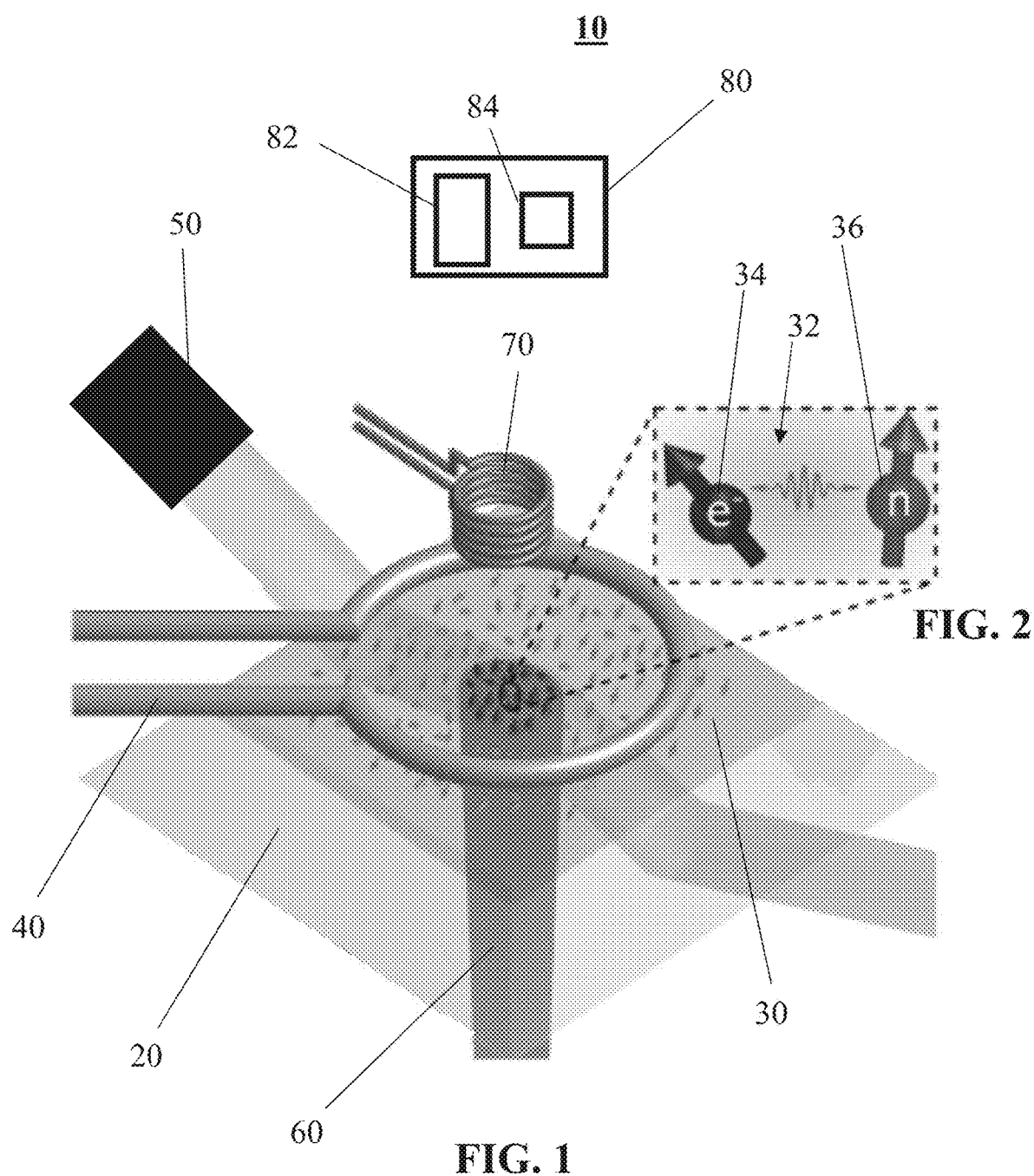
FIG. 1 is a schematic illustration of a nitrogen-vacancy (NV) center ensemble quantum sensing system in accordance with aspects of the present disclosure.
FIG. 2 is an enlarged, schematic illustration of the area of detail indicated in FIG. 1 showing the two-qubit system (electronic spin and nuclear spin) of each NV center of the ensemble.

Turning to FIGS. 1 and 2, a quantum sensor system 10 provided in accordance with the present disclosure includes a diamond chip 20 having an NV center ensemble layer 30, e.g., formed via chemical vapor deposition, irradiation, and annealing, or in any other suitable manner. The NV center ensemble layer 30 may define a thickness of 10 µm (or any other suitable thickness) and includes a plurality of NV centers 32. The number of NV centers 32 may be at least on the order of $10^4$ in aspects; in other aspects, at least on the order of $10^6$; in still other aspects, at least on the order of $10^8$; and, in yet other aspects, on the order of $10^9$. As noted above, each NV center 32 in the ensemble layer 30 forms a two-qubit system: a sensing/readout qubit (electronic spin states $m_s=0$ and $m_s=-1$ and corresponding qubit states $D_e$ and $U_e$) 34 and a memory qubit (nuclear spin states $m_I=-\frac{1}{2}$ and $m_I=\frac{1}{2}$ and corresponding qubit states $D_n$ and $U_n$) 36 that can be entangled to map information therebetween (see FIG. 2). An external magnetic bias field, e.g., an external DC magnetic bias field, is applied to system 10 along the NV symmetry axis. The magnetic bias field may be generated by a feedback-stabilized electromagnet or in any other suitable manner.

System 10 further includes an antenna 40 configured to deliver both MW and RF pulse signals. Antenna 40 is shown as a shorted single-loop coil (e.g., of 1 mm diameter) although other suitable antennae for both MW and RF pulse signal delivery, or separate antennae for MW and RF pulse signal delivery are also contemplated. The MW pulse signals are utilized to drive transition of the NV electronic spins while the RF pulse signals are utilized to drive transition of the nuclear spins. With momentary reference to FIG. 5, antenna 40, more specifically, may be connected to an MW source 42 and an RF source 44. Respective amplifiers 43, 45 amplify the MW and RF signals produced by MW source 42 and RF source 44, respectively. A power splitter is configured to receive both the MW and RF signals to enable transmission of both the MW and RF pulse signals to the antenna 40 for application to the delivery to the NV center ensemble layer 30 (FIG. 1).

Referring back to FIGS. 1 and 2, system 10 also includes a laser source 50 configured to deliver a light pulse, e.g., at 532 nm, to polarize the electronic spin states of the NV centers 32 in the ensemble layer 30 (see also FIGS. 3 and 4). An optical pulse is provided via laser source 50 prior to sensing (as noted above, to polarize the electronic spin states of the NV centers 32) as well as after mapping (entanglement and swapping) of the information contained in the electronic spin states to the nuclear spin states. The optical pulse after mapping functions to reset the electronic spin states of the NV centers 32. This allows the information stored in the nuclear spins to be repeatedly re-mapped (re-entangled and re-swapped) back onto the electronic spins and measured optically, thus providing plural readouts within a defined duration of time (which is limited by the nuclear spin lifetime of the system). Such repetitive readouts enable the detection of more photons over a longer amount of time, thus enhancing the overall readout fidelity.

A fluorescence sensor 60 of system 10 is configured to repetitively optically measure (readout) the electronic spin states of the NV centers 32 in the ensemble layer 30 (see also FIGS. 3 and 4), from which the magnetic field is determined. As illustrated in FIG. 1, a test coil 70 is utilized to provide the magnetic field to be sensed; of course, in practice, test coil 70 is replaced with the target signal to be sensed, such as a magnetic field signal originating, e.g., from NMR, integrated circuits, materials science, thermometry applications, etc.

Continuing to refer to FIG. 1, with respect to homogeneity, the external DC magnetic field applied to system 10 is controlled to provide a magnitude significantly different from 512 G (51.2 mT) in order to avoid the NV ground and excited state level crossing which dramatically reduces nuclear memory spin lifetime. In aspects, the magnitude of the external DC magnetic field is 370 mT (7× greater than 51.2 mT). Nuclear memory spin lifetime improves quadratically as the field increases from 51.2 mT, so higher magnitudes are generally preferred, e.g., at least 3×, at least 5×, or at least 7× greater than 51.2 mT). However, a significantly different magnitude from 51.2 mT, as utilized herein, includes any value above 60 mT or less than 40 mT.

The absolute bias magnetic field range is less than about 100 uT across the spatial extent of the NV centers 32 in the ensemble layer 30. This requirement comes from the need to selectively address the hyperfine split NV resonances individually. Ranges an order of magnitude smaller or multiple orders of magnitude smaller are also contemplated. The above-detailed magnetic field may be produced and shimmed in any suitable manner. With respect to temporal variations, the absolute bias magnetic field range is configured to drift over the course of a quantum sensing and repetitive readout protocol by less than 100 uT).

As the MW and RF pulses are applied globally to the NV center ensemble layer 30, system 10 is configured such that variation in the MW and RF pulses over the ensemble 30 is less than 6 dB such that high fidelity can be maintained.

With respect to optical pulses, although a wavelength of 532 nm of laser light is detailed herein, any other suitable wavelength of from about 500 nm to about 637 nm is contemplated, as wavelengths in this range are sufficient to repolarize the NV centers 32 into the ms=0 electronic ground state within a time of <5 ms (typically about 3-7 µs) determined by the nuclear spin lifetime of the NV centers 32. With regard to optical intensity, a Gaussian beam or a flat-top providing uniform illumination at sufficient brightness to repolarize the NV centers 32 without harming the nuclear spin lifetime of the NV centers 32 may be provided.

System 10 may further include at least one controller 80 having at least one processor 82, e.g., at least one quantum processor, and associated memory(s) 84, e.g., quantum memory(s), storing instructions to be executed by the processor(s) 82 to control application of the energy pulses (MW, RF, and optical), readout pulses, and magnetic field. In particular, the at least one controller 80 may implement the quantum sensing and repetitive readout protocol 600 detailed below (see FIG. 6) and/or any other aspects and features of the present disclosure detailed herein.

Figure 6:
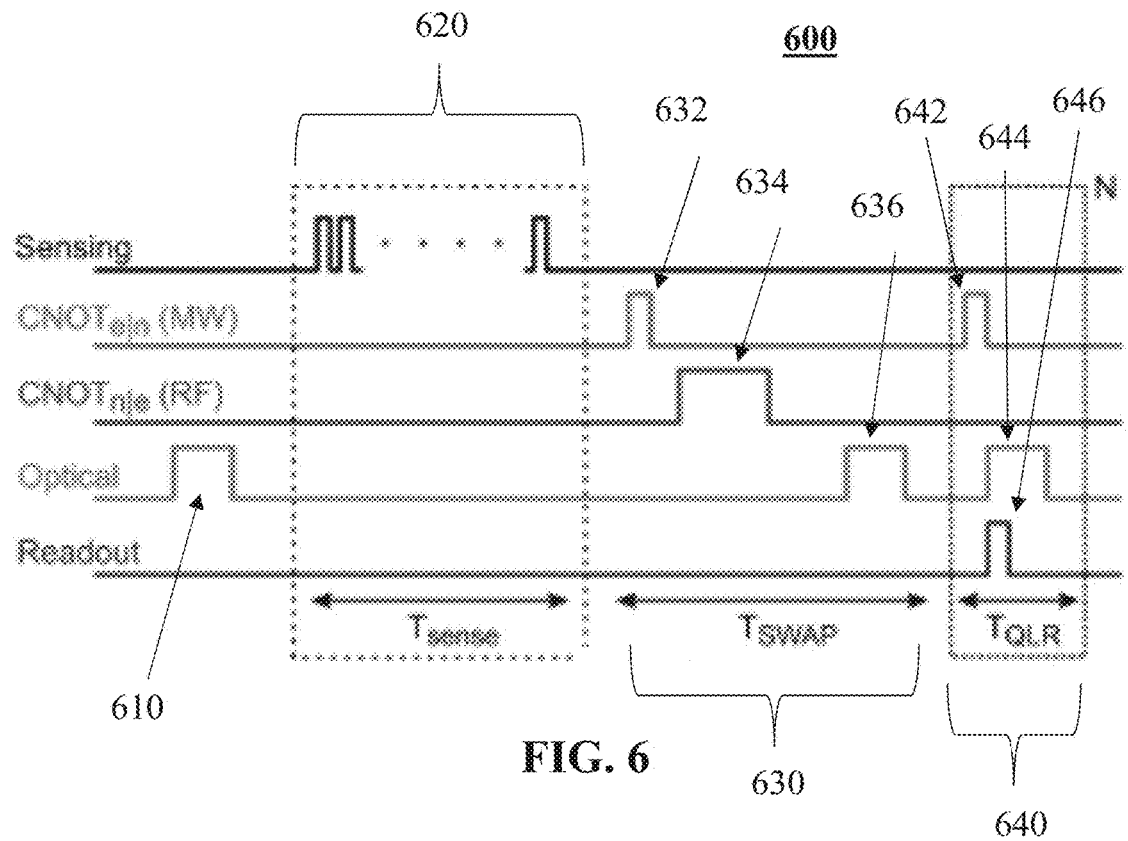
FIG. 6 is a graph illustrating a pulse sequence protocol for NV center ensemble quantum sensing in accordance with aspects of the present disclosure.

Referring to FIG. 6, a quantum sensing and repetitive readout protocol 600 in accordance with the present disclosure is described. Protocol 600 may be implemented using system 10 (FIG. 1) or any other suitable system. Further, protocol 600 is only exemplary, as it is contemplated that other suitable pulse configurations, sequences, and/or durations may be utilized in accordance with the aspects and features of the present disclosure.

Figure 7:
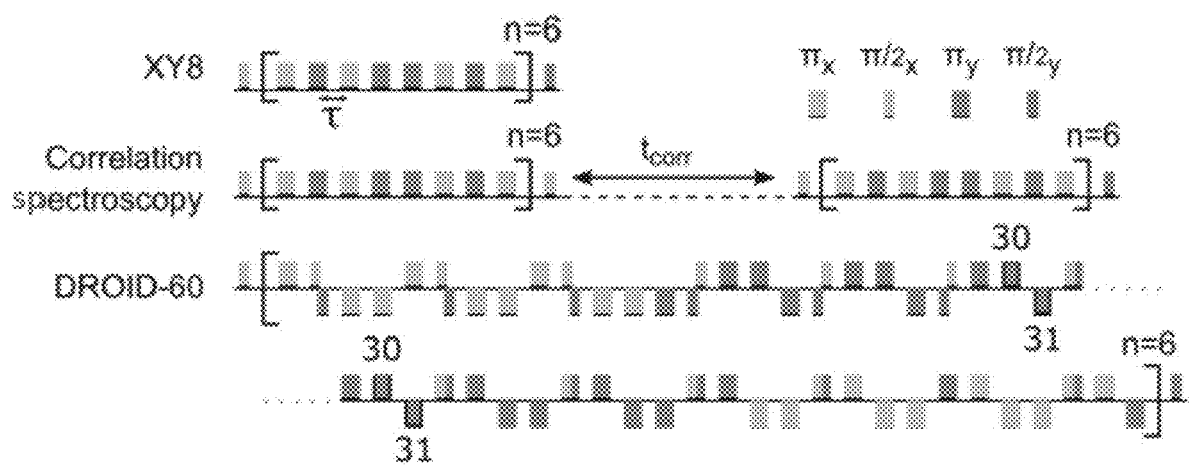
FIG. 7 illustrates exemplary AC magnetic field sensing sequences in accordance with aspects of the present disclosure.

Initially, in a preparation stage 610, a light pulse, e.g., at 532 nm, is provided to polarize the electronic spin states of the NV centers in the ensemble layer. In a subsequent sensing stage 620, a magnetic field sensing sequence is performed for a duration $T_{sense}$. The magnetic field sensing sequence may be configured for AC magnetic field sensing or DC magnetic field sensing. With momentary reference to FIG. 7, example AC magnetic field sensing sequences are shown: an XY 8:6 dynamical decoupling sequence (top); a correlation spectroscopy sequence (middle); and a DROID-60 decoupling sequence (bottom). Other suitable sensing sequences include, for example and without limitation, T1 relaxometry, Ramsey sequences, and strain-CPMG sequences (e.g., for sensing non-magnetic sources like lattice strain in the diamond, pressure, or temperature). The sensing sequence, in aspects, may include MW pulses, RF pulses, combined MW & RF pulses, optical pulses, combinations thereof, or any other suitable sensing sequence pulses. Regardless of the particular implementation, as a result of the magnetic field sensing sequence, the electronic spins of the NV centers reflect (obtain) information regarding the sensed magnetic field.

Turning back to FIG. 6, at the completion of the sensing stage 620, a swap stage 630 is performed wherein the sensed information captured in the electronic spin in each NV center in the ensemble is mapped (entangled and swapped) onto the nearby nuclear spin. The swap stage 630 operates for a duration $T_{swap}$. The swap stage 630 includes two controlled NOT (CNOT) gates. The first CNOT gate is an MW pulse 632 that exchanges the spin populations of the states $D_e$, $U_n$ and $U_e$, $U_n$. Thus, this MW pulse 632 acts as a CNOT operation on the electronic spin, conditioned on the nuclear spin state. The second CNOT gate is an RF pulse 634 that exchanges the spin populations of the states $U_e$, $U_n$ and $U_e$, $D_n$. As a result, the electronic spin population is mapped to that of the nuclear spin, thus encoding the information measured by the sensor spins (the electronic spins) onto the memory spins (the nuclear spins). The swap stage 630 concludes with an optical pulse 636 that, as mentioned above, resets the electronic spin states of the NV centers after the mapping (entanglement and swapping) has occurred.

Continuing with reference to FIG. 6, after the swap stage 630, a readout stage 640 is repeated a plurality of times, e.g., N times, over the course of a total duration defined by the nuclear spin lifetime. Each readout stage 640 includes application of an MW CNOT gate 642 which functions to map the information stored in the nuclear memory spins back to the electronic spins and, subsequently, an optical repolarization pulse 644 and a data acquisition readout pulse 646 (for optically measuring the electronic spins of the NV centers, enabling determination of the magnetic field based thereon). Repeating the readout stage 640 enables a larger number of readouts (e.g., as many readouts as can be performed within the duration defined by the nuclear spin lifetime). These plural readouts enhance the overall readout fidelity and allow for a high-precision average measurement of the sensor spin states of the ensemble. In aspects, the number of readouts is at least 250; in other aspects, at least 500; in yet other aspects, at least 1000; and in still other aspects, at least 1500.

Figure 8:
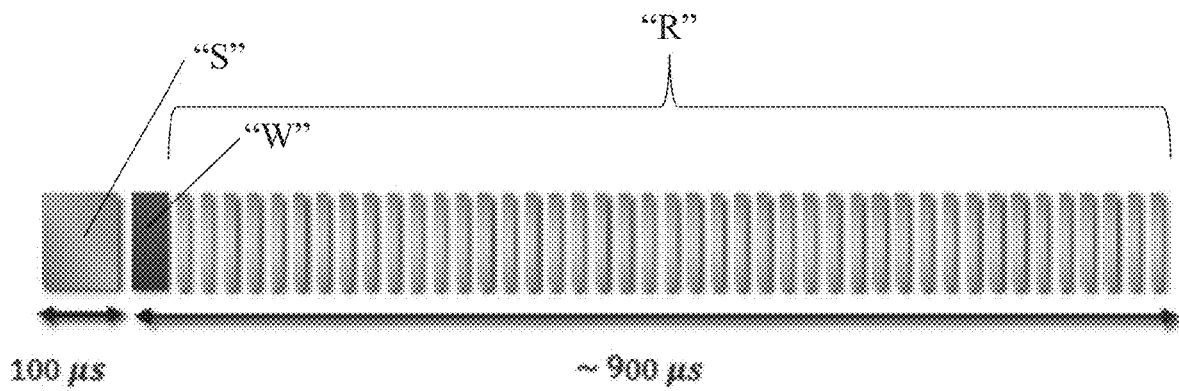
FIG. 8 is a schematic illustration of repetitive readout, from a single sensing sequence, of electronic spin in an NV center ensemble quantum sensing system in accordance with aspects of the present disclosure.
Figure 9:
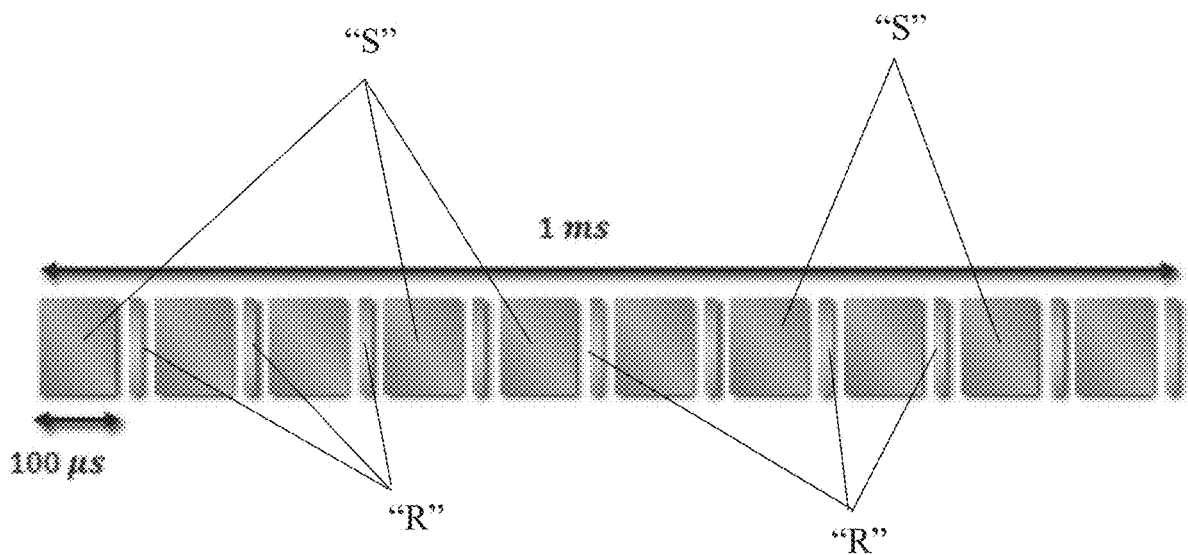
FIG. 9 is a schematic illustration of multiple consecutive sensing sequences and subsequent single readouts of electronic spin in accordance with the prior art.

FIGS. 8 and 9 contrastingly illustrate the number of repetitive readouts "R" after each sensing sequence "S" capable of being obtained using the systems and methods of the present disclosure (see FIG. 8) within a period of time, as compared to the single readout "R" following each sensing sequence "S" capable of being obtained using the systems and methods of the prior art (see FIG. 9) within the same period of time. For example, in accordance with the present disclosure, after a single sensing sequence "S" duration of 100 µs, followed by a swap sequence "W," over forty (40) readouts "R" may be obtained in a total readout duration of 1 ms since multiple readouts "R" are obtained after a single sensing sequence "S" and swap sequence "W" (see FIG. 8) whereas, with respect to the prior art, for the same sensing sequence "S" duration of 100 µs, only ten readouts "R" may be performed in the same total readout duration of 1 ms owing to the fact that a sensing sequence "S" is required prior to each readout "R" (see FIG. 9).

Figure 10:
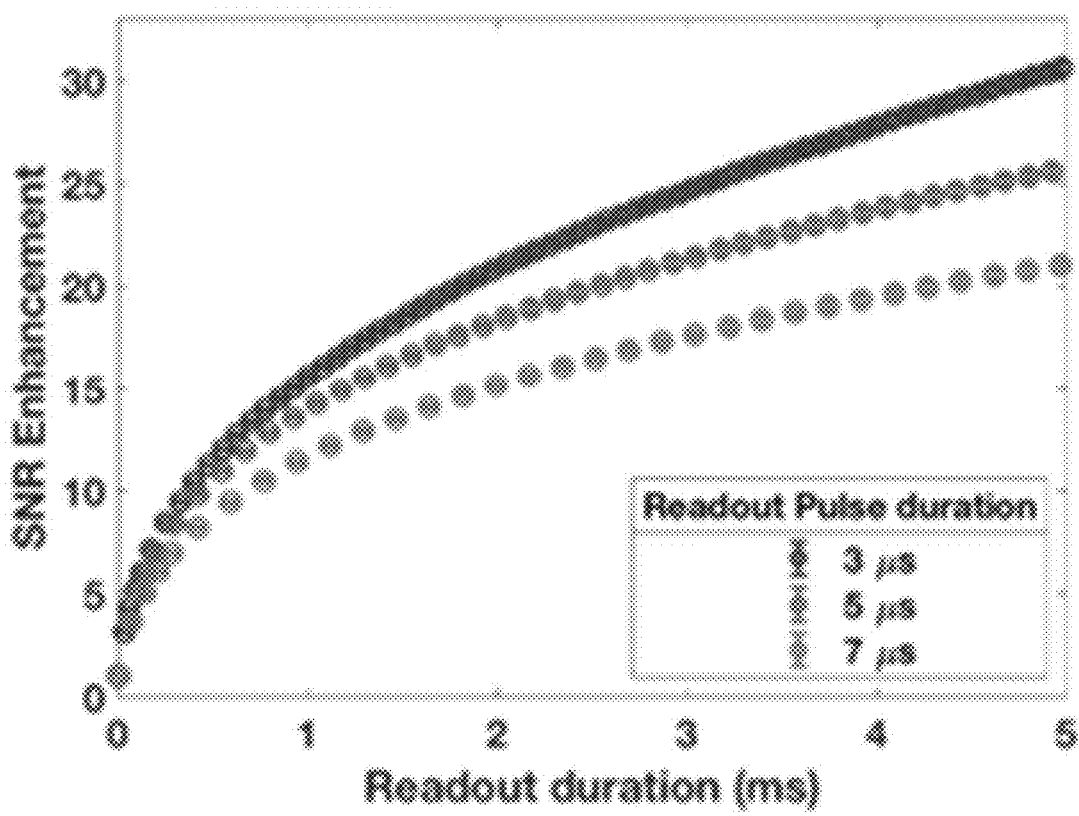
FIG. 10 is a graph illustrating signal to noise ratio enhancement as a function of overall readout duration for various different readout pulse durations in accordance with aspects of the present disclosure.

FIG. 10 illustrates experimental results of signal to noise ratio enhancement (compared to prior art systems and methods) as a function of overall readout duration for various different readout pulse durations in accordance with the systems and methods of the present disclosure. As shown, as the overall readout duration increases (thus enabling more readouts within the overall readout duration), the signal to noise ratio enhancement increases (before ultimately flattening out). Likewise, as more readouts within an overall readout duration can be obtained as the readout pulse duration is decreased (overall readout duration is defined as the readout pulse duration multiplied by the number of readouts), a greater signal to noise ratio enhancement is achieved for each successive shorter readout pulse duration. As shown, a signal to noise ratio enhancement approaching 30× can be achieved in accordance with the systems and methods of the present disclosure.

Figure 11:
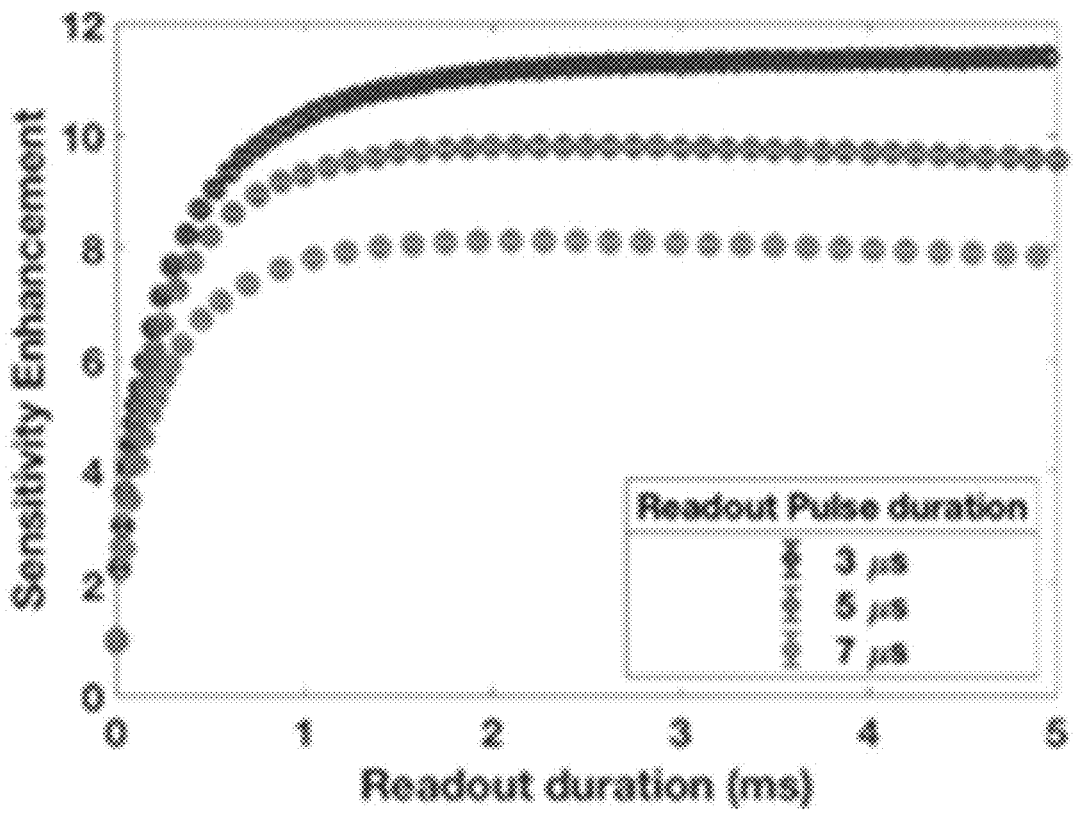
FIG. 11 is a graph illustrating sensitivity enhancement as a function of overall readout duration for various different readout pulse durations in accordance with aspects of the present disclosure.

FIG. 11 illustrates experimental results of sensitivity enhancement (compared to prior art systems and methods) as a function of overall readout duration for various different readout pulse durations in accordance with the systems and methods of the present disclosure. As shown, sensitivity enhancement is substantially maintained as the overall readout duration increases; indeed, the systems and methods of the present disclosure enable minimization of the slope of any decrease. As shown, a sensitivity enhancement greater than 10× can be achieved in accordance with the systems and methods of the present disclosure. At a greater than 10× sensitivity enhancement (corresponding to a 3 µs readout pulse duration) the signal to noise enhancement approaches 30× (see FIG. 10)).

It should be understood that the foregoing description is only illustrative of the present disclosure. Various alternatives and modifications can be devised by those skilled in the art without departing from the disclosure. Accordingly, the present disclosure is intended to embrace all such alternatives, modifications, and variances. The aspects described with reference to the attached drawings are presented only to demonstrate certain examples of the disclosure. Other elements, steps, methods, and techniques that are insubstantially different from those described above and/or in the appended claims are also intended to be within the scope of the disclosure.

What is claimed is:

1. A method of quantum sensing, comprising:
   obtaining information regarding a target signal in electronic spin states of quantum defects in an ensemble of quantum defects;
   mapping the information regarding the target signal from the electronic spin states of the quantum defects to corresponding nuclear spin states associated with the quantum defects;
   applying a light pulse to the ensemble of quantum defects to reset the electronic spin states of the quantum defects; and
   repeating a readout stage a plurality of times within a readout duration, wherein the readout stage includes:

mapping the information regarding the target signal back from the nuclear spin states to the corresponding electronic spin states; and applying a data acquisition readout pulse to optically measure the electronic spin states of the quantum defects.

2. The method according to claim 1, wherein obtaining the information includes:

applying a light pulse to the ensemble of quantum defects to polarize the electronic spin states of the quantum defects; and performing a sensing sequence to obtain the information regarding the target signal in the electronic spin states of the quantum defects.

3. The method according to claim 2, wherein the sensing sequence includes one of: an XY decoupling sequence; a correlation spectroscopy sequence; or a DROID-60 decoupling sequence.

4. The method according to claim 1, wherein mapping the information regarding the target signal from the electronic spin states of the quantum defects to the corresponding nuclear spin states associated with the quantum defects includes applying a microwave (MW) pulse and a radio frequency (RF) pulse to the ensemble of quantum defects.

5. The method according to claim 1, wherein mapping the information regarding the target signal back from the nuclear spin states to the corresponding electronic spin states includes applying an MW pulse to the ensemble of quantum defects.

6. The method according to claim 5, wherein the readout stage further includes, after applying the MW pulse, applying a light pulse to the ensemble of quantum defects to repolarize the electronic spin states of the quantum defects.

7. The method according to claim 1, further comprising determining the information regarding the target signal based upon the optical measuring in the plurality of readout stages.

8. The method according to claim 1, wherein the ensemble of quantum defects includes an ensemble of nitrogen vacancy (NV) centers in diamond.

9. The method according to claim 1, wherein the information regarding the target signal includes information regarding a magnetic field signal.

10. The method according to claim 9, wherein the information regarding the target signal includes information regarding an AC magnetic field signal.

11. The method according to claim 1, further comprising applying a magnetic bias field to the ensemble of quantum defects during the obtaining, the mapping, the applying, and the repeating.

12. The method according to claim 11, wherein the magnetic bias field has a magnitude at least three times 51.2 mT.

13. The method according to claim 11, wherein the magnetic bias field has a range of less than 100 uT.

14. The method according to claim 1, wherein the number of quantum defects in the ensemble of quantum defects is at least on the order of $10^4$.

15. A quantum sensor, comprising:
an ensemble of quantum defects; and
at least one controller including at least one processor and at least one associated memory storing instructions to be executed by the processor to cause the at least one controller to:

direct application of a sensing sequence of energy pulses to the ensemble of quantum defects to obtain information regarding a target signal in electronic spin states of quantum defects in an ensemble of quantum defects;

direct application of a microwave (MW) pulse and a radio frequency (RF) pulse to the ensemble of quantum defects to map the information regarding the target signal from the electronic spin states of the quantum defects to corresponding nuclear spin states associated with the quantum defects;

direct application of a light pulse to the ensemble of quantum defects to reset the electronic spin states of the quantum defects; and direct repetition of a readout stage a plurality of times within a readout duration, wherein, in the readout stage, the at least one controller is caused to:

direct application of an MW pulse to the ensemble of quantum defects to map the information regarding the target signal back from the nuclear spin states to the corresponding electronic spin states; and direct application of a data acquisition readout pulse to the ensemble of quantum defects to optically measure the electronic spin states of the quantum defects.

16. The quantum sensor according to claim 15, wherein the at least one controller is further caused to direct application of a light pulse to the ensemble of quantum defects to polarize the electronic spin states of the quantum defects prior to the sensing sequence.

17. The quantum sensor according to claim 16, wherein the at least one controller is further caused to direct application of a light pulse to the ensemble of quantum defects to repolarize the electronic spin states of the quantum defects after the MW pulse in each readout stage.

18. The quantum sensor according to claim 16, wherein the ensemble of quantum defects includes an ensemble of nitrogen vacancy (NV) centers in diamond.

19. The quantum sensor according to claim 16, wherein the information regarding the target signal includes information regarding a magnetic field signal.

20. The quantum sensor according to claim 16, wherein the at least one controller is further caused to direct application of a magnetic bias field to the ensemble of quantum defects at a magnitude at least three times 51.2 mT.

* * * * *